(12) United States Patent
Mansky (10) Patent No.: US 6,857,309 B2
(45) Date of Patent: Feb. 22, 2005

(54) HIGH THROUGHPUT MECHANICAL RAPID SERIAL PROPERTY TESTING OF MATERIALS LIBRARIES

(75) Inventor: Paul Mansky, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 128 days.

(21) Appl. No.: 10/225,942

(22) Filed: Aug. 22, 2002

(65) Prior Publication Data

US 2003/0097871 A1 May 29, 2003

Related U.S. Application Data

(60) Provisional application No. 60/314,842, filed on Aug. 24, 2001.

(51) Int. Cl.[7] .............................................. G01N 13/00
(52) U.S. Cl. .................... 73/64.49; 73/64.48; 73/64.51; 73/826; 73/863.01; 73/864.91
(58) Field of Search ....... 73/64.51, 64, 863.01–864.91, 73/64.48–64.52, 54.23, 24, 54.31, 41, 788, 796, 809, 826

(56) References Cited

U.S. PATENT DOCUMENTS

| | | |
|---|---|---|
| 1,870,412 A | 8/1932 | Kennedy |
| 3,071,961 A | 1/1963 | Heigl et al. |
| 3,675,475 A | 7/1972 | Weinstein |
| 3,713,328 A | 1/1973 | Aritomi |
| 3,798,960 A | 3/1974 | Glass |
| 3,805,598 A | 4/1974 | Corcoran |
| 3,818,751 A | 6/1974 | Karper et al. |
| 3,849,874 A | 11/1974 | Jeffers |
| 3,895,513 A | 7/1975 | Richardson |
| 3,908,441 A | 9/1975 | Virloget |
| 3,933,032 A | 1/1976 | Tschoegl |
| 4,229,979 A | 10/1980 | Greenwood |
| 4,447,125 A | 5/1984 | Lazay et al. |
| 4,517,830 A | 5/1985 | Gunn et al. |
| 4,567,774 A | 2/1986 | Manahan et al. |
| 4,570,478 A | 2/1986 | Soong |
| 4,599,219 A | 7/1986 | Cooper et al. |
| 4,602,501 A | 7/1986 | Hirata |
| 4,605,589 A | 8/1986 | Orphanides |
| 4,680,958 A | 7/1987 | Ruelle et al. |
| 4,685,328 A | 8/1987 | Huebner et al. |
| 4,699,000 A | 10/1987 | Lashmore et al. |
| 4,715,007 A | 12/1987 | Fujita et al. |
| 4,740,078 A | 4/1988 | Daendliker et al. |
| 4,749,854 A | 6/1988 | Martens |
| 4,789,236 A | 12/1988 | Hodor et al. |
| 4,793,174 A | 12/1988 | Yau |
| 4,829,837 A | 5/1989 | Telfer |

(List continued on next page.)

FOREIGN PATENT DOCUMENTS

| | | |
|---|---|---|
| DE | 198 45 867 A1 | 7/1999 |
| EP | 0 317 356 | 5/1989 |
| EP | 0 406 413 A1 | 1/1991 |

(List continued on next page.)

OTHER PUBLICATIONS

Woodward, Roger P., "A New Dynamic Contact Angle System (as presented at Pittcon 95)", Fist Ten Angstroms, pp. 1–8.

(List continued on next page.)

*Primary Examiner*—Edward Lefkowitz
*Assistant Examiner*—Alandra Ellington
(74) *Attorney, Agent, or Firm*—Dobrusin & Thennisch PC (57) ABSTRACT

A library of materials is screened for mechanical properties such as surface tension or interfacial tension. A library of materials is provided. A stimulus such as a stress or force is provided to each member of the library. A response (e.g., a resistance) of each of the materials due to the stimulus is measured and the response, the stimulus or both are recorded and related to provide data. Thereafter, the data is analyzed to reach conclusions regarding the material samples.

23 Claims, 3 Drawing Sheets

U.S. PATENT DOCUMENTS

| | | |
|---|---|---|
| 4,893,500 A | 1/1990 | Fink-Jensen |
| 4,899,575 A | 2/1990 | Chu et al. |
| 4,899,581 A | 2/1990 | Allen et al. |
| 4,914,966 A | 4/1990 | White, Jr. et al. |
| 4,932,270 A | 6/1990 | Lurie et al. |
| 4,975,320 A | 12/1990 | Goldstein et al. |
| 5,008,081 A | 4/1991 | Blau et al. |
| 5,051,239 A | 9/1991 | von der Goltz |
| 5,092,179 A | 3/1992 | Ferguson |
| 5,115,669 A | 5/1992 | Fuller et al. |
| 5,142,900 A | 9/1992 | Duke |
| 5,193,383 A | 3/1993 | Burnham et al. |
| 5,236,998 A | 8/1993 | Lundeen et al. |
| 5,269,190 A | 12/1993 | Kramer et al. |
| 5,271,266 A | 12/1993 | Eschbach |
| 5,272,912 A | 12/1993 | Katsuzaki |
| 5,280,717 A | 1/1994 | Hoseney et al. |
| 5,303,030 A | 4/1994 | Abraham et al. |
| 5,305,633 A | 4/1994 | Weissenbacher et al. |
| 5,365,776 A | 11/1994 | Lehmann et al. |
| 5,398,885 A | 3/1995 | Andersson et al. |
| 5,437,192 A | 8/1995 | Kawamoto et al. |
| 5,438,863 A | 8/1995 | Johnson |
| 5,452,614 A | 9/1995 | Kato et al. |
| 5,452,619 A | 9/1995 | Kawanabe et al. |
| 5,481,153 A | 1/1996 | Turner |
| 5,517,860 A | 5/1996 | Lin et al. |
| 5,520,042 A | 5/1996 | Garritano et al. |
| 5,532,942 A | 7/1996 | Kitamura et al. |
| 5,610,325 A | 3/1997 | Rajagopal et al. |
| 5,626,779 A | 5/1997 | Okada |
| 5,699,159 A | 12/1997 | Mason |
| 5,700,953 A | 12/1997 | Hlady et al. |
| 5,723,792 A | 3/1998 | Miyazaki |
| 5,728,532 A | 3/1998 | Ackley |
| 5,756,883 A | 5/1998 | Forbes |
| 5,764,068 A | 6/1998 | Katz et al. |
| 5,776,359 A | 7/1998 | Schultz et al. |
| 5,817,947 A | 10/1998 | Bergerus |
| 5,821,407 A | 10/1998 | Sekiguchi et al. |
| 5,847,268 A | 12/1998 | Ball |
| 5,847,283 A | 12/1998 | Finot et al. |
| 5,877,428 A | 3/1999 | Scolton |
| 5,892,157 A | 4/1999 | Syre |
| 5,922,967 A | 7/1999 | Motoyama |
| 5,959,297 A | 9/1999 | Weinberg et al. |
| 5,985,356 A | 11/1999 | Schultz et al. |
| 5,999,887 A | 12/1999 | Giannakopoulos et al. |
| 6,004,617 A | 12/1999 | Schultz et al. |
| 6,010,616 A | 1/2000 | Lewis et al. |
| 6,013,199 A | 1/2000 | McFarland et al. |
| 6,024,925 A | 2/2000 | Little et al. |
| 6,030,917 A | 2/2000 | Weinberg et al. |
| 6,033,913 A | 3/2000 | Morozov et al. |
| 6,034,240 A | 3/2000 | La Pointe |
| 6,034,775 A | 3/2000 | McFarland et al. |
| 6,040,193 A | 3/2000 | Winkler et al. |
| 6,043,317 A | 3/2000 | Mumick et al. |
| 6,043,363 A | 3/2000 | LaPointe et al. |
| 6,045,671 A | 4/2000 | Wu et al. |
| 6,050,138 A | 4/2000 | Lynch et al. |
| 6,050,139 A | 4/2000 | Bousfield et al. |
| 6,087,181 A | 7/2000 | Cong |
| 6,092,414 A | 7/2000 | Newman |
| 6,124,476 A | 9/2000 | Guram et al. |
| 6,149,882 A | 11/2000 | Guan et al. |
| 6,151,123 A | 11/2000 | Nielsen |
| 6,157,449 A | 12/2000 | Hajduk |
| 6,175,409 B1 | 1/2001 | Nielsen et al. |
| 6,177,528 B1 | 1/2001 | LaPointe et al. |
| 6,182,499 B1 | 2/2001 | McFarland et al. |
| 6,187,164 B1 | 2/2001 | Warren et al. |
| 6,203,726 B1 | 3/2001 | Danielson et al. |
| 6,225,487 B1 | 5/2001 | Guram |
| 6,225,550 B1 | 5/2001 | Hornbostel et al. |
| 6,230,548 B1 | 5/2001 | Han et al. |
| 6,242,623 B1 | 6/2001 | Boussie et al. |
| 6,248,540 B1 | 6/2001 | Weinberg et al. |
| 6,260,407 B1 | 7/2001 | Petro et al. |
| 6,265,226 B1 | 7/2001 | Petro et al. |
| 6,265,601 B1 | 7/2001 | Guram et al. |
| 6,268,513 B1 | 7/2001 | Guram et al. |
| 6,294,388 B1 | 9/2001 | Petro |
| 6,296,771 B1 | 10/2001 | Miroslav |
| 6,306,658 B1 | 10/2001 | Turner et al. |
| 6,315,923 B1 | 11/2001 | Devenney et al. |
| 6,326,090 B1 | 12/2001 | Schultz et al. |
| 6,336,353 B2 | 1/2002 | Matsiev et al. |
| 6,393,895 B1 | 5/2002 | Matsiev et al. |
| 6,393,898 B1 | 5/2002 | Hajduk et al. |

FOREIGN PATENT DOCUMENTS

| | | |
|---|---|---|
| EP | 1 158 290 A2 | 11/2001 |
| JP | 402297040 A | 12/1990 |
| WO | WO 93/13400 | 7/1993 |
| WO | WO 96/11878 | 4/1996 |
| WO | WO 98/15501 | 4/1998 |
| WO | WO 99/18431 | 4/1999 |
| WO | WO 00/17413 | 3/2000 |
| WO | WO 00/23921 | 4/2000 |
| WO | WO 00/36410 A1 | 6/2000 |
| WO | WO 00/40331 | 7/2000 |
| WO | WO 00/51720 | 9/2000 |
| WO | WO 00/67086 | 11/2000 |
| WO | WO 01/22058 A1 | 3/2001 |
| WO | WO 01/53798 A1 | 7/2001 |
| WO | WO 01/79949 A2 | 10/2001 |

OTHER PUBLICATIONS

Woodward, Ph.D., Roger P., "Contact Angle Measurements Using the Drop Shape Method", First Ten Angstroms, pp. 1–8.

Woodward, Ph.D., Roger P., "Surface Tension Measurements Using the Drop Shape Method", First Ten Angstroms, pp. 1–6.

Woodward, Ph.D., Roger P., "Dynamic Surface Tension and Dilational Stress Measurements Using the Drop Shape Method", First Ten Angstroms, pp. 1–6.

Woodward, Ph.D., Roger P., "Two–Dimensional Contact Angle and Surface Tension Mapping (As presented at Pittcon 96)", First Ten Angstrom, pp. 1–6.

Woodward, Ph.D., Roger P., "Prediction of Adhesion and Wetting from Lewis Acid Base Measurements (As presented at TPOs in Automotive 2000)", First Ten Angstroms, pp. 1–6.

"FTA2000 Automated Surface Energy Analyzer", Product Brief, First Ten Angstroms, Jun. 1998.

"Low Interfacial Tension Measurements", Application Notes, First Ten Angstroms, Aug. 14, 2000.

"Sessile Drop Interfacial Tension Measurements", Application Notes, First Ten Angstroms, Nov. 2, 2000.

"Influence of Drop's Volume on Contact Angle", Application Notes, First Ten Angstroms, Aug. 15, 2000.

"A Simple Introduction to the Laplace Equation", Application Notes, First Ten Angstroms, Dec. 11, 2000.

"Determining t=0 in Contact Angle Measurements", Application Notes, First Ten Angstroms, Nov. 10, 1997.

"Contact Angle Accuracy", Application Notes, First Ten Angstroms, Jun. 29, 1998.

"Do I Need a Contact Angle Analyzer?", Application Notes, First Ten Angstroms, pp. 1–5.

"Dyne Solution Equivalents", Application Notes, First Ten Angstroms, Aug. 17, 2000.

"Cleanliness Measurements Using Contact Angles", Application Notes, First Ten Angstroms, Aug. 14, 2000.

"Basic Contact Angle Measurements on Paper", Application Notes, First Ten Angstroms, Oct. 16, 1997.

"Surface Tension Measurements Polymers, Waxes, and Solders", Application Notes, First Ten Angstroms, Aug. 18, 1997.

"Treated Mylar Contact Angle Measurements", Application Notes, First Ten Angstroms, Nov. 2, 2000.

"Contact Angles on Lens", Application Notes, First Ten Angstroms, Apr. 5, 2000, pp. 1–6.

"What are Contact Angles?", First Ten Angstroms, Sep. 11, 1997.

"DMA 2980 Dynamic Mechanical Analyzer,"http://www.tainst.com/dma2.html, Dec. 29, 2000.

"Introducing the New DMTA V!", http://www.rheometric-scientific.com/dmtaV.htm, Dec. 29, 2000.

"Standard Test Method for Rubber Property–Intrenational Hardness," American Society for Testing and Materials.

Amitay–Sadovsky, Ella and H. Daniel Wagner, "Evaluation of Young's Modulus of Polymers from Knoop Microindentation Tests" Polymer Communications, 1998, vol. 39, No. 11, pp. 2387–2390.

Calleja, F.J. Balta, "Microhardness Studies of Polymers and Their Transitions" TRIP, Dec. 1994, vol. 2, No. 12, pp. 419–425.

Bowlt, C., "A Simple Capillary Viscometer" Physics Education, Mar. 1975, vol. 10, No. 2, pp. 102–103.

Lacombe, Robert H. and Jeremy Greenblatt, "Mechanical Propoerties of Thin Polyimide Films" pp. 647–668.

Shinozaki, D.M. and Y. Lu, "Micro–Indentation Relaxation Measurements in Polymer Thin Films" Journal of Electronic Materials, 1997, vol. 26, No. 7, pp. 852–858.

Wierenga, P.E. and A.J.J. Franken, "Ultramicroindentation Apparatus for the Mechanical Characterization of Thin Films" J. Appl. Phys., Jun. 15, 1984, 55 (12).

European Search Report dated Dec. 10, 2001.

International Search Report dated Dec. 4, 2002.

Odian, Principles of Polymerization, 3rd Ed., John Wiley & Sons, Inc. (1991).

Young, W.C., Roark's Formulas for Stress and Stain. 1989.

Timoshenko, S., Theory of Plates and Shells, McGraw–Hill, New York 1940.

Osterberg, Peter M. and Stephen D. Senturia, "M–TEST: A Test Chip for MEMS Material Property Measurement Using Electrostatically Actuated Test Structures," Journal of Microelectromechanical Systems, vol. 6, No. 2, Jun. 1997.

Kim, J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223–228.

Grover, G. et al., "A Screening Technique for Fabric Handle", J. Text. Inst., 1993, 84 No. J. Textile Institute, pp. 486–494.

Pan, Ning and K.C. Yen, "Physical Interpretations of Curves Obtained Through the Fabric Extraction Processss for Handle Measurement," Textile Research Journal 62(5), pp. 279–290 (1992).

"Handle–O–Meter", Thwing–Albert Instrument Company, Philadelphia, PA.

Raeel, Mastura and Jiang Liu, "An Empirical Model for Fabric Hand" Textile Research Journal 62, 1, pp. 31–38 (1991).

Ali S.I. and Shahida Begum, "Fabric Softeners and Softness Perception", Ergonomics, v.37, No. 5, pp. 801–806 (1994).

U.S. Appl. No. 09/420,334 entitled " Graphic Design of Combinatorial Material Libraries" (Lacy, et al.) filed Oct. 18, 1999.

U.S. Appl. No. 09/305,830 titled "Synthesizing Combinatorial Libraries of Materials" (Rust, et al.) filed May 5, 1999.

U.S. Appl. No. 09/550,549 entitled "Automated Process Control And Data Management System And Methods" (Crevier, et al.) filed Apr. 14, 2000.

U.S. Appl. No. 09/755,623 entitled "Laboratory Database System and Methods For Combinatorial Materials Research" (Dorsett, Jr., et al.) filed Jan. 5, 2001.

The family of applications for U.S. Appl. No. 09/227,558 entitled, "Apparatus and Method of Research for Creating and Testing Novel Catalysts, Reactions and Polymers" (Turner et al.) filed Jan. 8, 1999.

U.S. Appl. No. 09/235,368 entitled "Polymerization Method From the Combinatorial Synthesis and Analysis of Organometallic Compounds and Catalysts" (Weinberg et al.) filed Jan. 21, 1999.

U.S. Provisional Appl. No. 60/122,704 entitled "Controlled, Stable Free Radical Emulsion and Water–Based Polymerizations" (Klaerner et al.) filed Mar. 9, 1999.

The family of applications for U.S. Appl. No. 09/567,598 entitled "Polymer Libraries on a Substrate, Method for Forming Polymer Libraries on a Substrate and Characterization Methods with Same" (Boussie et al.) filed May 10, 2000.

The family of applications for U.S. Appl. No. 09/174,856 titled "Graphic Design of Combinatorial Material Libraries" (Lacy, et al.) filed on Oct. 19, 1998.

The family of applications for U.S. Appl. No. 09/156,827 entitled "Formation of Combinatorial Arrays of Materials Using Solution–Based Methodologies" (Giaquinta et al.) filed Sep. 18, 1998.

U.S. Appl. No. 09/579,338 entitled "Rheo–Optical Indexer and Method of Screening and Characterizing Arrays of Materials" (Carlson et al.) filed May 25, 2000.

U.S. Appl. No. 09/939,404 entitled "High Throughput Mechanical Property and Bulge Testing of Material Libraries," (D. Hajduk et al.) filed Aug. 24, 2001.

U.S. Appl. No. 09/939,252 entitled "High Throughput Mechanical Rapid Serial Property Testing of Material Libraries," (P. Mansky) filed Aug. 24, 2001.

U.S. Appl. No. 09/939,139 entitled "High Throughput Fabric Handle Screening," (M. Kossuth et al.) filed Aug. 24, 2001.

U.S. Appl. No. 09/939,149 entitled "High Throughput Rheological Testing of Materials," (P. Mansky et al.) filed Aug. 24, 2001.

U.S. Appl. No. 09/939,263 entitled "High Throughput Mechanical Property Testing of Materials Libraries Using Capacitance," (D. Hajduk et al.) filed Aug. 24, 2001.

The family of applications for U.S. Appl. No. 09/580,024 entitled "Instrument for High Throughput Measurement of Material Physical Properties and Method of Using Same," (Carlson, et al.) filed May 26, 2000.

U.S. Appl. No. 09/938,994 entitled "High Throughput Mechanical Property Testing of Material Libraries Using a Piezoelectric," (D. Hajduk) filed Aug. 24, 2001.

U.S. Provisional Appl. No. 60/371,357 filed Apr. 10, 2002.

U.S. Appl. No. 10/133,938 filed Apr. 26, 2002.

HIGH THROUGHPUT MECHANICAL RAPID SERIAL PROPERTY TESTING OF MATERIALS LIBRARIES

This application claims the benefit of U.S. Provisional Application No.:
APPLICATION No. 60/314,842
FILING DATE Aug. 24, 2001

TECHNICAL FIELD

The present invention generally relates to the field of materials characterization or materials testing. In particular, the invention relates to high throughput rapid serial screens for evaluating properties such as surface tension, interfacial tension and the like of libraries of polymers or other materials.

BACKGROUND OF THE INVENTION

Currently, there is substantial research activity directed toward the discovery and optimization of materials for a wide range of applications. Although the chemistry of many materials, including polymers and polymerization reactions has been extensively studied, nonetheless, it is rarely possible to predict a priori the physical or chemical properties a particular material will possess or the precise composition and architecture that will result from any particular synthesis scheme. Thus, characterization or testing techniques to determine such properties are an essential part of the discovery process.

Combinatorial materials science refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

The characterization or testing of polymers or other materials using combinatorial methods has only recently become known. Examples of such technology are disclosed, for example, in commonly owned U.S. Pat. No. 6,182,499 (McFarland et al); U.S. Pat. No. 6,175,409 B1 (Nielsen et al); U.S. Pat. No. 6,157,449 (Hajduk et al); U.S. Pat. No. 6,151,123 (Nielsen); U.S. Pat. No. 6,034,775 (McFarland et al); U.S. Pat. No. 5,959,297 (Weinberg et al), all of which are hereby expressly incorporated by reference herein. However, as combinatorial materials science becomes more accepted, a need exists to rapidly test or characterize a wider variety of properties. The above-cited references do not disclose every possible test that might be performed in the research and development of materials for a specific desired application.

For example, a nee exists for combinatorial methods and apparatuses for synthesizing or otherwise providing polymers and other materials followed by screening of those materials in an array format for physical or mechanical characteristics such as surface tension, interfacial tension and the like. Conventional instruments and methods for synthesis and screening of the materials for mechanical properties are generally inadequate to handle the types and numbers of samples. For example, conventional instruments and other apparatuses lack the ability to screen mechanical properties of several materials in rapid succession, in parallel, on a single substrate or a combination thereof. Thus, challenges are presented for creating systems and methods that can quickly process and test (either in parallel or in serial succession) mechanical properties of many materials. Additionally, combinatorial or high-throughput methods that create material samples must be processed at a similar rate and conventional instruments are inadequate for forming, processing or otherwise treating materials so that the materials are in appropriate condition for high throughput screening of mechanical properties. This invention meets these challenges and the inadequacies of the prior art for certain properties of materials.

SUMMARY OF THE INVENTION

In accordance with one preferred embodiment of the present invention, a method for screening an array of materials for a material property is provided. According to the method a library of at least four sample materials is provided. Each of the at least four sample materials is subjected to one or more forces in opposition to a tension of each of the at least four sample materials. A response of each of the at least four sample materials to the one or more forces is monitored. Moreover, the response of the each of the at least four materials is correlated to the tensions of each of the at least four sample materials.

In accordance with another preferred embodiment of the present invention, a method for measuring tension of a plurality of sample materials is provided. According to the method, a library comprising at least four different sample materials is provided. Thereafter a tension of each of the at least four different sample materials is serially measured at a throughput rate no greater than about 5 minutes per sample material.

DETAILED DESCRIPTION OF THE PREFERRED EMBODIMENT

I. Glossary

The following terms are intended to have the following general meanings as they are used herein.

1. Substrate: A material having a rigid or semi-rigid surface. In many embodiments, at least one surface of the substrate will be substantially flat, although in some embodiments it may be desirable to physically separate synthesis regions for different materials with, for example, dimples, wells, raised regions, etched trenches, or the like. In some embodiments, the substrate itself contains wells, raised regions, etched trenches, etc. which form all or part of the synthesis regions. According to other embodiments, small beads or pellets may be provided on the surface within dimples or on other regions of the surface or, alternatively, the small beads or pellets may themselves be the substrate. The substrate will typically have a surface area of about 1 to 400 cm$^2$, usually about 6 to 100 cm$^2$. However, it should be understood that the substrate may be substantially smaller or larger than these ranges depending on the particular application. For example, the substrate may have a surface area as small as about 0.1 to 1 cm$^2$, or as large as about 1 to 100. One preferred substrate useful in accordance with the present invention is a microtiter plate having a plurality of wells, and preferably at 96×N wells, where N is an integer, one or larger.

2. Predefined Region: A predefined region is a localized area on a substrate which is, was, or is intended to be used for formation of a selected resulting material and is otherwise referred to herein in the alternative as "known" region, "reaction" region, a "selected" region, or simply a "region." The predefined region may have any convenient shape, e.g., linear, circular, rectangular, elliptical, wedge-shaped, etc. Additionally, the predefined region, can be a bead or pellet which is coated with component(s) of interest. In this embodiment, the bead or pellet can be identified with a tag, such as an etched binary bar code that can be used to indicate the history of the bead or pellet, i.e., to identify which components were deposited thereon. In some embodiments, a predefined region and, therefore, the area upon which each distinct material is placed for screening is smaller than about 25 cm$^2$, less than 10 cm$^2$, less than 5 cm$^2$, even more less than 1 cm$^2$, still more less than 1 mm$^2$, and less than 0.5 mm$^2$. In most preferred embodiments, the regions have an area less than about 10,000 um$^2$, less than 1,000 u m$^2$, less than 100 u m$^2$, and less than 10 u m$^2$.

3. Mixture: The term "mixture" refers to a collection of molecules, ions, electrons, chemical substances, etc. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

4. Viscosity: A measure of a resistance of a fluid to flow when subjected to a force, and preferably one for inducing a shear stress. Reference herein to viscosity is not intended to exclude the employment of viscosity measurements to the determination of other rheological properties recognized as interdependent upon the measurement of viscosity, including but not limited to, density, temperature dependent properties of materials such as melt flow index, or the like.

5. Surface Tension: A measure of the force (e.g., intermolecular forces) acting on the surface of a liquid tending to minimize the surface area of the liquid. Surface tension may be quantified in terms of the force acting over the surface per unit area of the surface perpendicular to the surface or in terms of free energy per unit interfacial area.

6. Interfacial Tension: A measure of the force (e.g., intermolecular forces) acting on the surface of a liquid tending to minimize the surface area of the liquid while in another liquid. Interfacial tension may be quantified as the force acting over the surface per unit length of the surface.

As noted herein, the definition of surface tension includes interfacial tension, however, the reverse in not always true (i.e., interfacial tension refers to the tension at the interface between two liquids whereas, surface tension applies to tension at the interface of a liquid in and any other medium such as a fluid, gas, liquid or solid).

These and other aspects of the invention are to be considered exemplary and non-limiting, and are discussed in greater detail below. The several aspects of the characterization methods and systems disclosed and claimed herein can be advantageously employed separately, or in combination to efficiently characterize a variety of materials, with particular emphasis on solid materials, polymeric materials, liquid materials or flowable materials. In preferred embodiments, these features are employed in combination to form a materials characterization system that can operate as a high-throughput screen in a combinatorial materials science research program directed to identifying and optimizing new materials. Such materials appropriate for combinatorial research may include, for instance, polymers, catalysts, products of various polymerization reaction conditions, lubricants, gels, adhesives, coatings and/or products of new post-synthesis processing conditions. Other materials appropriate for combinatorial research according to the present invention may include, but are not limited to, foodstuffs, cosmetics, beverages, lotions, creams, pharmaceuticals, inks, mucus, fuels, additives, detergents, surfactants, shampoos, conditioners, dyes, waxes, fuel cell electrolytes, photoresist, semiconductor material, wire coatings, hair styling products and the like.

Combinatorial Approaches for Science Research

In a combinatorial approach for identifying or optimizing materials or reactions, a large compositional space (e.g., in the context of polymers; of monomers, comonomers, catalysts, catalyst precursors, solvents, initiators, additives, or of relative ratios of two or more of the aforementioned) or a large reaction condition space (e.g., of temperature, pressure and reaction time) may be rapidly explored by preparing libraries and then rapidly screening such libraries.

For example, in the context of polymers (but also applicable to other materials), combinatorial approaches for screening a polymer library can include an initial, primary screening, in which polymerization products are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.).

Once one or more hits have been satisfactorily identified based on the primary screening, polymer and polymerization product libraries focused around the primary-screen hits can be evaluated with a secondary screen—a screen designed to provide (and typically verified, based on known materials, to provide) chemical composition or process conditions that relate with a greater degree of confidence to commercially-important processes and conditions than those applied in the primary screen.

In general, the systems, devices and methods of the present invention may be applied as either a primary, secondary or other screen, depending on the specific research program and goals thereof. Bulk quantities of a particular material may be made after a primary screen, a secondary screen, or both.

Figure 1:
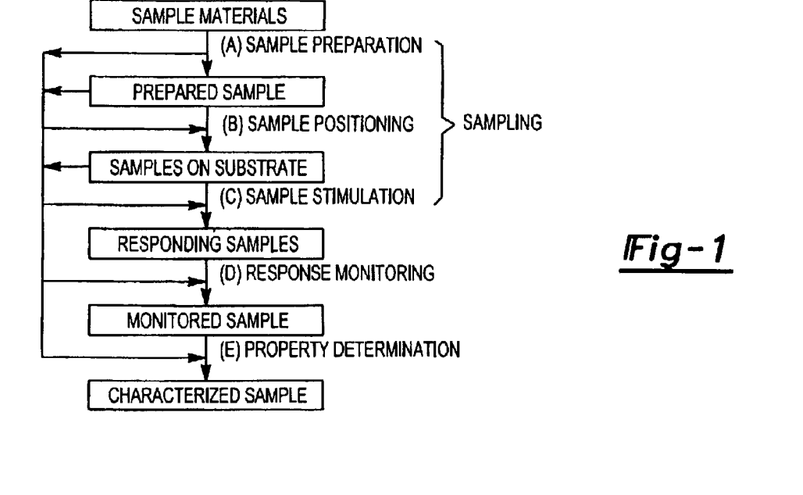
FIG. 1 is a flowchart of possible steps for methods of the present invention.

Referring to FIG. 1, the systems and methods, preferably, start with a library or array of sample materials that may exhibit one or more predetermined physical/mechanical properties. Ultimately, these predetermined properties will be determined in a determination step (Step E), however, several prior steps may be effected prior to Step E. The sample materials may be prepared such as by heating, cooling, or addition of additives. Such preparation is typically designed to affect the properties that are ultimately being determined. The sample materials may also be positioned in a desirable manner for property determination. The materials may be positioned on a substrate, a machine or otherwise positioned to assist in ultimately determining properties of the materials.

It will be appreciated that one of the advantageous features of the present invention is that it affords the ability to screen newly created materials some or all of which are uncharacterized or whose properties are unknown prior to the time of screening. Thus, previously unidentified and uncharacterized new materials can be screened for a common selected property. However, this does not prevent the employment of known references controls or standard as among the library members.

It shall be recognized that sample preparation (Step A) and sample positioning (Step B) may be optional steps in property determination protocols. Also sample preparation and sample positioning may be performed in any order if they are performed. Additionally it should be recognized that sequences other than the order of steps listed above are possible, and the above listing is not intended as limiting.

Typically, however, stimulation of the sample materials (Step C) is needed to effect one or more responses of the materials wherein the responses are related to the one or more physical properties that are being tested. Exemplary stimuli include force, contact, motion and the like. Exemplary responses include flow, or resistance to flow, deflection, adhesion, deformation, rupture or the like. Negative forces (e.g., compression as opposed to tension, negative pressure as opposed to positive pressure) or the like may be employed.

The responses of the materials are typically monitored (Step D) with hardware such as sensors, transducers, load cells or other like devices. Properties may be determined (Step E) quantitatively or qualitatively by relating the responses to the material properties.

A plurality of samples may be characterized as described above in connection with FIG. 1. As a general approach for improving the sample throughput for a plurality of samples, each of the steps (A) through (E) of FIG. 1 applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

A characterization protocol for a plurality of samples can involve a single-step process (e.g., direct measurement of a property of a sample or of a component thereof) or several steps. In a rapid-serial screen approach for a single-step process, the plurality of samples and a single measuring instrument or other instruments are serially positioned in relation to each other for serial analysis of the samples. In a parallel analysis approach, (e.g., as might be employed by itself, or in an upstream or downstream analysis of the samples relative to a rapid-serial analysis of the present invention) two or more measuring instruments or other apparatus are employed to measure properties of two or more samples simultaneously.

In a serial-parallel approach, a property of a larger number of samples (e.g., four or more) is screened as follows. First, a property of a subset of the four or more samples (e.g., 2 samples) is screened in parallel for the subset of samples, and then serially thereafter, a property of another subset of four or more samples is screened in parallel. It will be recognized, of course, that plural measuring instruments can be employed simultaneous, or plural measuring instruments can be employed serially.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series.

Sample Materials

The samples for which the present invention is useful for screening include polymeric materials or any other liquid, flowable or solid material that is capable of being provided as a liquid, solid, gel or other suitable form. Accordingly, without limitation, pure materials, mixtures of materials, bulk materials, particles of materials, thin films of materials, dispersions of materials, emulsions of materials, and solutions of materials are all contemplated as within the useful scope of the present invention.

In a particularly preferred embodiment, the present invention is employed for screening polymer samples, or plastic samples including polymers.

In one embodiment, the polymer molecule of the polymer component is preferably, but need not be, a non-biological polymer. A non-biological polymer is, for purposes herein, a polymer other than an amino-acid polymer (e.g., protein) or a nucleic acid polymer (e.g., deoxyribonucleic acid (DNA)). However, the employment of the present invention for screening of materials for use as biological implants or prosthetics is contemplated. For instance, the ability of a biological polymer to bind to an agent may be determined from the mechanical property response of a sample of the material in the presence of such agent.

The particular composition of the polymer molecule is not critical. The material may be thermoplastic, thermoset or a mixture thereof. It may be a polycondensate, polyadduct, a modified natural polymer. Exemplary materials include polymers incorporating olefins, styrenes, acrylates, methacrylates, polyimides, polyamides, epoxies, silicones, phenolics, rubbers, halogenated polymers, polycarbonates, polyketones, urethanes, polyesters, silanes, sulfones, allyls, polyphenylene oxides, terphthalates, or mixtures thereof. Other specific illustrative examples can include repeat units or random occurrences of one or more of the following, without limitation: polyethylene, polypropylene, polystyrene, polyolefin, polyamide, polyimide, polyisobutylene, polyacrylonitrile, poly(vinyl chloride), poly(methyl methacrylate), poly(vinyl acetate), poly (vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of polymers. Exemplary naturally-occurring polysaccharides include cellulose, dextran, gums (e.g., guar gum, locust bean gum, tamarind xyloglucan, pullulan), and other naturally-occurring biomass. Exemplary semisynthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of effects of variations of additives upon the characteristics of the material. The various components of the heterogeneous polymer sample can be uniformly or non-uniformly dispersed in the continuous fluid phase.

In one preferred embodiment, the polymer samples of the present invention are melted or otherwise heated to a fluid state, with the resulting material constituting a liquid sample. Heating may be performed simultaneously while the samples are on a common substrate. Alternatively, the samples might be heated to a liquid state and then transferred (e.g., manually or with an automated sampler) to a common substrate, where it is heated to maintain its liquid state.

In another embodiment at a point prior to, during, or after depositing the sample onto the substrate, the polymer sample is preferably, chemically treated to form a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 1 nm to about 500 nm, more typically from about 5 nm to about 300 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 um to about 1000 $\mu$m, more typically from about 0.4 $\mu$m to about 500 $\mu$m, and even more typically from about 0.5 $\mu$m to about 200 $\mu$m. Exemplary polymers that can be in the form of neat polymer samples include dendrimers, and siloxane, among others. The liquid polymer sample can also be employed in the form of a slurry, a latex, a microgel, a physical gel, or in any other form sufficient for creating an array for screening analysis as described and claimed herein. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semicrystalline or amorphous), a glassy state or rubbery state. The polymer sample can, regardless of its particular form, have various attributes, including variations with respect to polarity, solubility and/or miscibility.

It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g. temperature moisture, radiation, chemicals, etc.), aged, or the like.

Sample Size

The sample size is not narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 100 milligrams, even more typically from about 5 micrograms to about 1000 micrograms, and still more typically from about 20 micrograms to about 50 micrograms.

If and when placed on a substrate for forming a library, as discussed herein with regard to sampling, the samples may be dispensed with any suitable dispensing apparatus (e.g. an automated micropipette or capillary dispenser, preferably with a heated tip). Each sample of the library is dispensed to an individually addressable region on the substrate. Preferably each sample occupies no more than about 1000 mm$^2$ of area on a substrate surface, more preferably no more than about 100 mm$^2$, and even more preferably no more than about 10 mm$^2$. In applications where the sample is disposed in a well, preferably the sample size does not exceed about 1000 milligrams.

Accordingly, for dispensing fluid samples, the individual samples are each dispensed in amounts no greater than about 100 ml, more preferably no greater than about 10 ml and still more preferably no greater than about 1 ml.

Libraries of Sample Materials

Libraries of samples have 2 or more samples that are physically or temporally separated from each other—for example, by residing in different regions of a common substrate, in different sample containers of a common substrate, by having a membrane or other partitioning material positioned between samples, or otherwise. The plurality of samples preferably has at least 4 samples and more at least 8 samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. For screening of polymers or other materials the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples or more, and preferably from about 8 samples to about 10,000 or more samples. In many applications, however, the number of samples can range from about 80 samples to about 1500 samples.

A library of samples comprises two or more different samples spatially separated—preferably, but not necessarily on a common substrate, or temporally separated. Candidate samples (i.e., members) within a library may differ in a definable and typically predefined way, including with regard to chemical structure, processing (e.g., synthesis) history, mixtures of interacting components, post-synthesis treatment, purity, etc. The samples are spatially separated, preferably at an exposed surface of the substrate, such that the library of samples is separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. The use of reference standards, controls or calibration standards may also be performed, though it is not necessary. Further, a library may be defined to include sub-groups of members of different libraries, or it may include combinations of plural libraries.

Typically, however, for combinatorial science research applications, at least two or more, preferably at least four or more, even more preferably eight or more and, in many cases, most preferably each of the plurality of polymer samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of said samples included in said library are different from each other. Still more preferably, the library includes at least 48 samples and at least 90% of said samples included in the library are different from each other.

The substrate can be a structure having a rigid or semi-rigid surface on which or into which the library of samples can be formed, mounted, deposited or otherwise positioned. The substrate can be of any suitable material, and preferably includes materials that are inert with respect to the polymer samples of interest, or otherwise will not materially affect the mechanical or physical characteristics of one sample in an array relative to another. Exemplary polymeric materials that can be suitable as a substrate material in particular applications include polyimides such as Kapton™., polypropylene, polytetrafluoroethylene (PTFE) and/or polyether etherketone (PEEK), among others. The substrate material is also preferably selected for suitability in connection with known fabrication techniques. Metal or ceramic (e.g., stainless steel, silicon, including polycrystalline silicon, single-crystal silicon, sputtered silicon, and silica ($SiO_2$) in any of its forms (quartz, glass, etc.)) are also preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Another suitable substrate is a silicon wafer that has been patterned to define a predetermined configuration on which the sample or samples are deposited (e.g., suspended deflectable arms). As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In certain preferred embodiments, the substrate is formed to securely maintain contact with a plurality of samples. According to various methodologies it may be desirable to place forces on samples while the samples remain secured to the substrate. Forces may be applied to the samples by one or more members separate from the substrate or the substrate may apply the forces.

Non-Polymer Sample Materials

Some aspects of the invention can have applications involving non-polymer samples, non-polymer elements or compounds can include organic or inorganic pigments, carbon powders (e.g., carbon black), metals, metal compounds, metal oxides, metal salts, metal colloids, metal ligands, etc., without particular limitation. Other materials, which may be characterized according to the present invention include, without limitation, ceramic materials, semiconducting and conducting materials, metal and composites. Still other materials for which the present application finds untility are discussed elsewhere herein.

Sampling/Auto-Sampler

Sampling of sample materials may be accomplished with a plurality of steps which include withdrawing a sample from a sample container and delivering at least a portion of the withdrawn sample to a substrate such as a microtiter plate. Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semiautomatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

Analytical Systems and Methods

According to the present invention, one or more systems, methods or both are used to determine the mechanical properties of a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Figure 2:
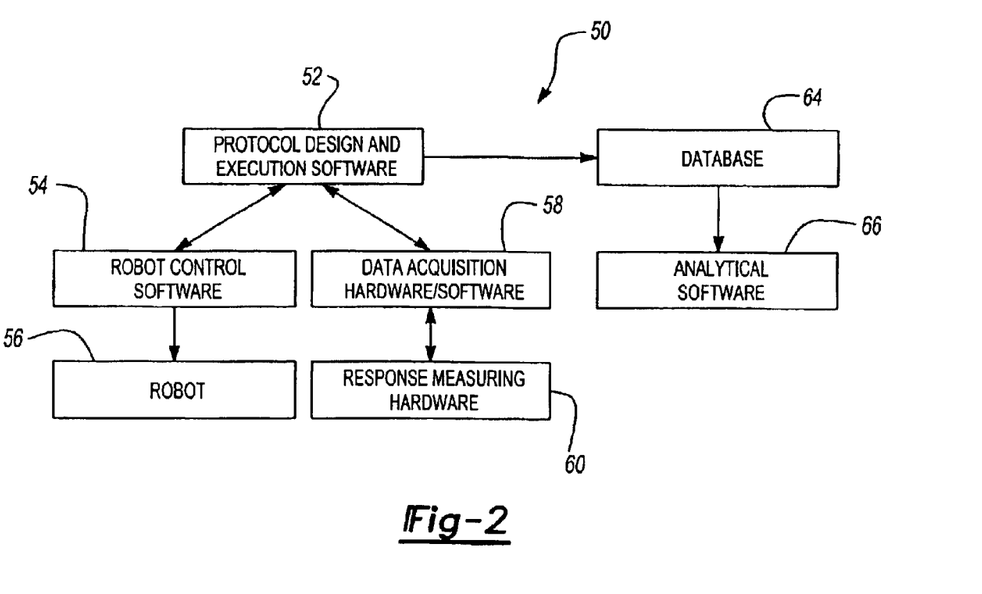
FIG. 2 is a block diagram of a potential platform system for executing methods and for operating systems.

Referring to FIG. 2, there is a flow schematic diagram of an exemplary automated system 50 for rapid determination of mechanical properties of several samples of material. Generally, the system 50 includes a suitable protocol design and execution software 52 that can be programmed with information such as synthesis, composition, location information or other information related to a library of materials positioned with respect to a substrate. The protocol design and execution software is typically in communication with robot control software 54 for controlling a robot 56 or other automated system. The protocol design and execution software 52 is also in communication with data acquisition hardware/software 58 for collecting data from response measuring hardware 60. Preferably, the robot control software 54 commands the robot 56 to apply stimuli to sample materials to evoke a response from the materials. At substantially the same time, the response measuring hardware 60 (e.g., sensors, transducers, load cells and the like) monitors the responses of the materials, the stimuli being applied to the materials or both and provides data on the responses to the data acquisition hardware/software 58. Thereafter, the robot control software 54, the data acquisition hardware/software 58 or both transmit data to the protocol design and execution software 52 such that the sample materials or information about the sample materials may be matched with their responses to the applied stimuli and transmitted at data to a database 64. Once the data is collected in the database, analytical software 66 may be used to analyze the data, and more specifically, to determine mechanical properties of the sample materials, or the data may be analyzed manually.

In a preferred embodiment, the system is driven by suitable software, such as LIBRARY STUDIO™, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.) or a combination thereof. Moreover, data collected or produced by the system may be viewed using other suitable software such as POLYVIEW™, by Symyx Technologies, Inc. (Santa Clara, Calif.). The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. application Ser. No. 09/420,334 filed on Oct. 18, 1999, U.S. application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands to control movement of the robot, for controlling activity at such individual address.

Figure 4:
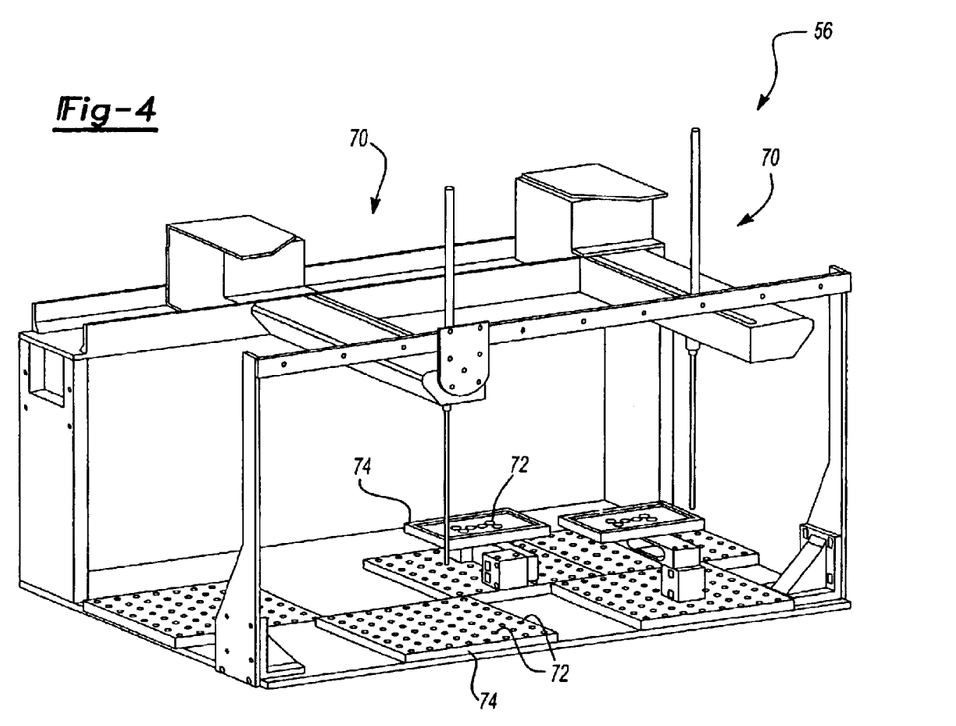
FIG. 4 is an exemplary automated apparatus or system for assisting in determining mechanical properties in accordance with the present invention.

In FIG. 4, there is illustrated one exemplary automated robot or apparatus 56 that may be operated using the system 50 of FIG. 2. As shown in FIG. 4, the apparatus 56 includes a pair of robot arms 70 appropriate for manipulating sample materials 72 located upon substrates 74.

Many of such aspects of the invention can be directly translated for use with parallel, serial or serial-parallel protocols. In a most preferred embodiment, for example, a rapid serial force system and protocols for that system can be used for characterization of materials with very high sample throughput.

Surface and Interfacial Tension

The systems and methods of the present invention include the ability to determine intrinsic properties exhibited by members of a library of materials such as surface tension, interfacial tension or both. According to one embodiment of the invention, members of the library are subjected to one of more forces in opposition to tensions of the materials. Responses of materials to such forces are monitored. Thereafter, the surface or interfacial tensions, or the cohesiveness of the materials are determined based upon the forces, responses or both.

Preferably, the sample materials are fluid and more preferably the materials are liquid. The forces may be applied to the materials by physical contact, by gravity or otherwise. The forces may be increasing or decreasing, they may ramp up or step up or they may be continuous. The forces may overcome the resistances exhibited by the tensions of the materials such as by separating a portion of each material from the remainder of the material or by expanding the exposed surface area of the sample material (e.g., by expanding a fluid such as air within the material samples). Alternatively, the forces may come to equilibrium with the resistances exhibited by the tensions of the materials such as by allowing a liquid to rest upon a surface of a substrate such that the surface tension (e.g., the cohesive forces) of the material samples are in equilibrium with the interfacial tension (e.g., adhesive forces) between the material samples and the substrate.

The forces may be compressive, tensile or shear. The force may be applied directly to the fluid or by manipulating the fluid such that the force may be otherwise supplied such as by gravity. The forces may be applied using one or more than one member or device for exerting one or more than one force on each sample. Alternatively, one member or device may exert one or more forces on a plurality of samples.

Responses of the materials are typically forces supplied by the tensions of the materials acting in directions opposing the forces being applied to the materials. For example, the response of each of the materials may be a resistance to the expansion of the surface area of the material. The resistances may be monitored by monitoring the forces being applied as compared to the resistances of the sample material to those forces (e.g., by monitoring whether the amount of force being supplied is overcoming the resistance of the material). One or more sensors may be used to monitor each sample. Alternatively, one or more sensors may be used to monitor a plurality of samples.

According to one preferred embodiment, the forces cause or initiate the separation of one portion of a sample material from the remainder of the sample material. Even more preferably, the separation of the materials occurs at known cross-sections of the materials such that the tensions may be determined by dividing either the forces or the resistances of the materials to the forces by the known cross-sections.

Figure 3A:
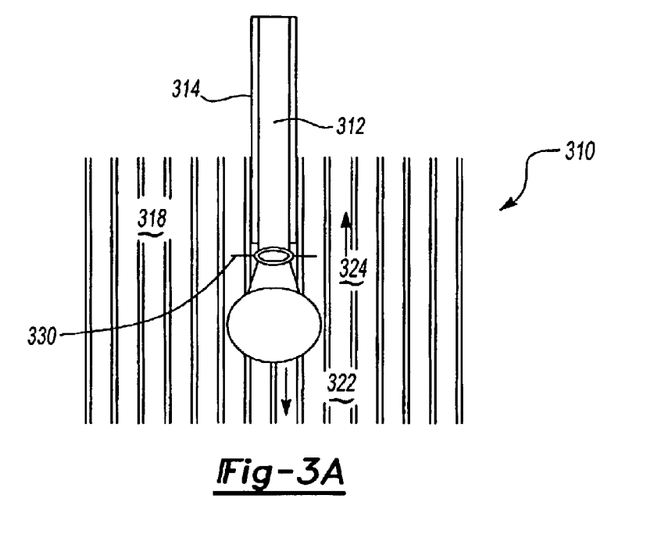
FIGS. 3(a)–3(d) are schematics of systems for assisting in determining mechanical properties of materials in accordance with the present invention.
Figure 3B:
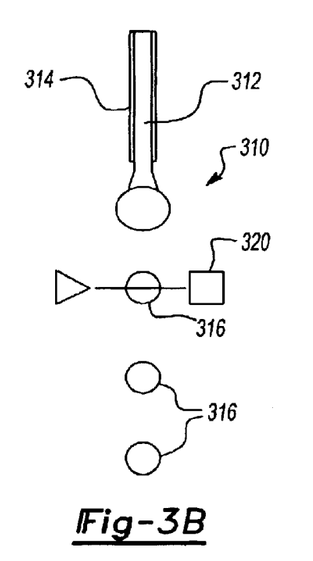

Referring to FIGS. 3(a)–3(b), there is illustrated a system 310 for measuring surface tension, interfacial tension or both of a library of fluid sample materials 312 according to a preferred embodiment. The system 310 includes one or more capillary tubes 314 for dispensing a fluid material 312 in drops 316 or otherwise through a fluid medium 318 (e.g., air or another fluid) past a photodetector 320. Preferably, the capillary tube 314 is attached to a robot or other automated system (not shown) so that the tube 314 may automatically retrieve portions of sample materials 312 to be dispensed in drops 316.

Retrieval of the sample materials 312 with the capillary tube 314 may be achieved according to a variety of protocols. Preferably, a pressure or force urges each sample material 312 into the capillary tube 314. The pressure or force may be provided by inducing a partial vacuum within the capillary tube 314 while an opening of the tube 314 is submerged in a sample material 312 such as by suction or otherwise. Alternatively, the downward force that is provided as the capillary tube 314 is submerged within a sample material 312 may urge the sample material into the capillary tube 314.

Once the sample material 312 is within the capillary tube 314, the tube 314 may be moved to a location wherein the sample material 312 is subjected to a force causing the sample material 312 to drip or otherwise flow past the photodetector 320 or another sensor. The force causing the sample material 312 to flow past the sensor 320 may be provided by overpressure within the capillary tube 314, by gravity or otherwise.

In the preferred embodiment, the pressure within the capillary tube 314 is brought into equilibrium with the pressure (e.g., atmospheric) surrounding the tube 314 such that drops 316 of fluid material 312 leave the capillary 314 when a downward gravitational force ($F_1$) 322 acting upon the forming drop 316 exceeds an upward force ($F_2$) 324 provided by surface or interfacial tension (y) of the fluid sample 312. Notably, tension (y) as used herein substantially represents surface tension when the medium 318 through which the drop 316 is dispensed is a relatively light gas such as air or a vacuum. However, the symbol (y) substantially represents interfacial tension when the medium 318 is a liquid or relatively heavier fluid.

The upward force ($F_2$) is calculated at a planar circular portion 330 of the fluid sample 312 that connects the forming drop 316 and the remainder of the fluid sample 312 in the capillary tube 314 according to the following equation:

$$F_2 = 2\Pi r y$$

wherein (r) represents the radius of the circular portion 330, which may be substantially approximated as the radius of the inner diameter of the capillary. The downward force ($F_1$) is calculated according to the following equation:

$$F_1 = g V \Delta \rho$$

wherein (g) is acceleration due to gravity, and $\Delta \rho$ is the difference in density between the fluid sample 312 and the medium 318 into which the sample 312 is dispensed (e.g., $\Delta \rho$ is substantially the density of the fluid sample 312 when the drops 316 are dispensed into a vacuum or a lighter gas medium 318 such as air). V is a measure of drop volume, and may be related to volumetric flow rate (Q) of the sample material from or through the capillary tube 314 by the equation:

$$V = Q \Delta t$$

wherein $\Delta t$ is the time interval between drops 316 passing the photodetector 320, which may be monitored according to any computerized or other system receiving signals from the photodetector. Moreover, the volumetric flow rate (Q) of the sample material 312 leaving the capillary tube 314 may be monitored by measuring the total volume of sample material 312 leaving the tube 314 divided by the total time that the sample material 312 is leaving the tube 314. Alternatively, the volumetric flow rate (Q) may be monitored by using a capillary tube 314 and system that dispenses a predetermined volume of sample material 312 and dividing that predetermined volume by the total time of dispensing the volume. Other methods of monitoring flow rate or even drop volume may also be utilized.

Thus, according to these equations, surface or interfacial tension (y) may be calculated algebraically according to the equation:

$$y = g Q \Delta t \Delta \rho / 2 \Pi r.$$

Figure 3C:
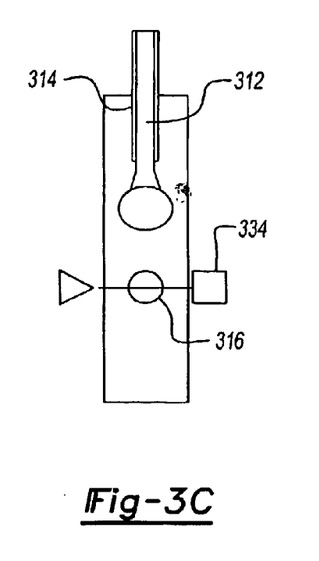

Referring to FIG. 3(c), there is illustrated a system 332 for determining interfacial tension wherein the fluid medium 318 through which the drops 316 are dispensed is another liquid wherein an optical detector 334 is used to detect the drops 316.

Figure 3D:
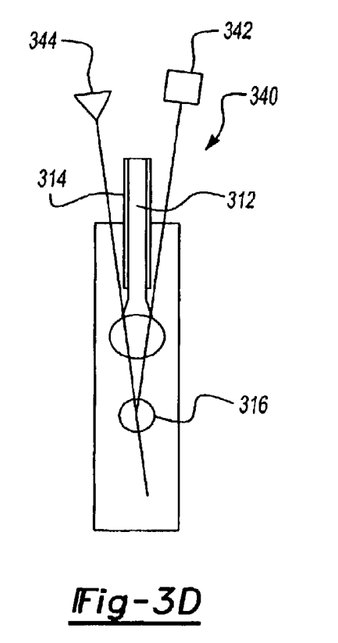

In another alternative system 340, referring to FIG. 3(d), an optical sensor 342 may be used in conjunction with light scattered from a light source 344 to determine interfacial tension (y) by detecting temporal changes (+or −) in the scattered light due to droplet 316 passage. Advantageously, drops 316 may be dispensed as desired (e.g., upward, sideways or downward) so long as they pass through the light provided by the light source 344 such that the optical sensor 342 can detect the scattered light.

To test an entire library of sample materials, only one capillary tube may be used to withdraw or move each sample material or a plurality of capillary tubes may be used to move the sample materials. For example, one automated system (e.g., a robotic arm) may manipulate or move one capillary tube and serially raise each sample material above a sensor for monitoring the flow rate of the sample material leaving the capillary tube. As an alternative example, two or more automated systems may be operated in parallel each moving its own capillary tube. Regardless of the number of automated systems used to move the one or more capillary tubes, it may be desirable to intermittently wash and/or dry the capillary tube in between retrievals of different sample materials such that any remnants of the previous sample material do not effect the testing of the next sample material. Alternatively, capillary tubes may be intermittently replaced in between retrievals of different sample materials for the same purpose.

According to another preferred embodiment, the forces are applied to the material samples by gravity, another member or a combination thereof. In the particular embodiment, the force or forces applied to the material samples preferably come to equilibrium with the forces supplied by the surface tension or cohesion of the material samples. Once at equilibrium, the surface tension or cohesion of the material samples may be determined from the response exhibited by the material sample to bring itself to equilibrium.

Figure 5:
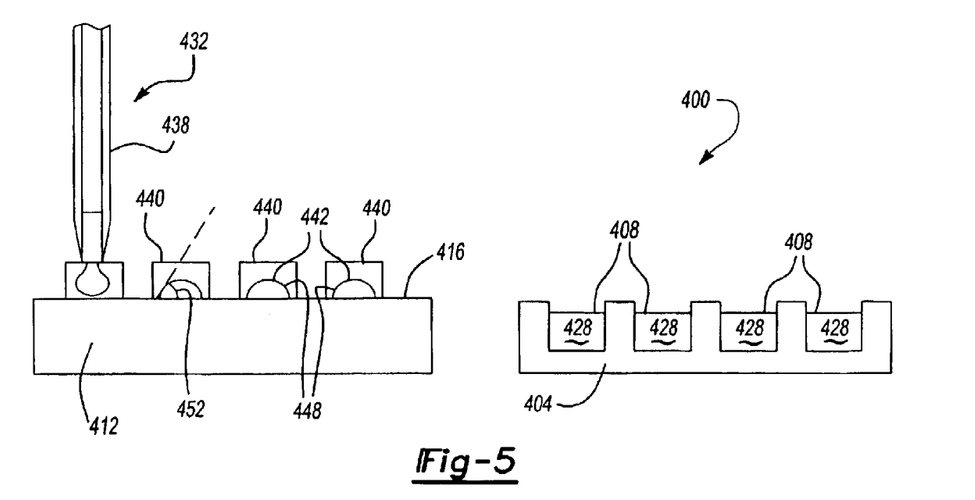
FIG. 5 is another exemplary system for assisting in determining mechanical properties in accordance with the present invention.

As an example and referring to FIG. 5, there is illustrated a system 400 including a first substrate 404 having a plurality of wells 408 and a second substrate 412 having a surface 416 that is preferably substantially horizontal and level. Preferably, the first substrate 404 supports a combinatorial library of material samples 428. As shown, the system 400 includes a dispenser 432 for dispensing portions of the material samples 428 onto the surface 416 of the substrate 412. In the preferred illustrated embodiment, the dispenser 432 includes a dispensing tube 438 such as a pipette, which can preferably dispense one drop of a liquid at a time. For dispensing, the dispensing tube 438 is preferably attached and movable by an automated system as previously described. It is also preferable for the system 400 to include one or more transducers 440.

In the preferred embodiment, the dispenser 432 dispenses one or more drops 442 of each material sample 428 of the library upon the surface 416 of the substrate 412. Shortly thereafter, the surface tension or cohesive forces of the drops 442 preferably come to equilibrium with a gravitational force that is continuously exerted upon the drops 442 and an interfacial tension or adhesive force exerted upon the drops 442 by the substrate 412. Preferably, both gravity and interfacial tension tend to at least partially attract the drops 442 to the substrate 412. As an equilibrium response, the drops 442 form their outer exposed surfaces 448 into spherical or dome shapes and each of the exposed surfaces 448 forms a contact angle 452 with the surface 416 of the substrate 412.

Preferably, the equilibrium response of drops 442 is monitored via the one or more transducers 440. It is contemplated that a plurality of transducers 440 are provided wherein each of the transducers 440 monitors one or more drops 442 as shown in FIG. 5. In such an embodiment, the transducers 440 are preferably mounted upon or adjacent the substrate 412. Alternatively, one transducer may monitor each of the drops 442. In such an embodiment, it may be preferable to mount the transducer 440 upon or adjacent to the tip 454 of the dispensing tube 438 such that the transducer 440 may monitor the drop 442 shortly after it has been dispensed. Alternatively, it may be advantageous to mount the transducer 440 adjacent to the tip 454 such that the transducer 440 can monitor a previously dispensed drop 442 while dispensing a new drop 442. For monitoring the response of the drops 442, it is preferable for the one or more transducers 440 to be optical sensors for sensing the shape of the drops 442 and particularly the shape of the outer surfaces 448 of the drops.

After monitoring the response of the drops 442, the response can be correlated to the surface tension of the drops 442 and therefore the surface tension of the material samples 428. In the preferred embodiment, the contact angle 452 can be readily determined from the shape of the drops 442. Once the contact angle 452 has been determined, the surface tension of the drops 442 can be determined according to a variety of art known techniques.

According to still other embodiments, it is contemplated that surface tension or interfacial tension of a library of material samples may be measured by expanding one fluid within another. For example, and without limitation, one or more tubes or tips thereof may be submerged in each member of a library of material samples followed by at least partially releasing or expanding one or more gas bubbles (e.g., air bubbles) in each of the samples. Thereafter, the pressure used to form the one or more bubbles (e.g., to a particular size) may be correlated to surface tension of the samples.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

A sample-throughput of 10 minutes per sample or less is important for a number of reasons. Systems that detect a property of a sample or of a component thereof at the aforementioned sample throughput rates can be employed effectively in a combinatorial research program. From a completely practical point of view, the characterization rates are also roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools™ PPR-48™ (Symyx Technologies, Santa Clara, Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data.

Additionally, as shown in connection with the examples provided herein, the characterization of polymer samples at such throughputs can offer sufficiently rigorous quality of data, to be useful for scientifically meaningful exploration of the material compositional and/or reaction conditions research space.

Hence, the average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently screen a polymer sample or component thereof having a particularly desired property (e.g., such as weight-average molecular weight). In short, the search can be accelerated for the particular property of research interest.

Calibration Methods and Standards

As desired the systems and methods of the present invention may optionally employ a calibration procedure. By way of example, a calibration standard is provided having a number of subcomponents that differ with respect to interfacial or surface tension of a material. Such subcomponents are typically referred to as "known standards" or, simply, "standards" that are well characterized with respect to the calibrating property of interest. They are analyzed by the measuring apparatus of the present invention and the apparatus is adjusted as desired.

The accuracy and precision of the determination of material properties can vary depending on the type of measurement being conducted, the purpose of the measurements and the like. According to one embodiment the response, the stimulus or both applied to each of the material samples of the samples may be ranked or indexed and the ranked or indexed properties may be compared with each other. In such a case, accuracy and precision with regard to determining exact values of the properties of the sample materials may not be as important as assuring that the tests are performed consistently upon samples that are compared to each other since the object of the testing may be to determine which materials perform best rather than determining exact material properties. In other cases, such as when the stimuli and responses of the sample materials will be used to compare the sample materials to known properties of known materials, it may be more important to determine values for sample material properties such as interfacial tension, surface tension and the like that are closer to the absolute values of those properties for the sample materials to allow useful comparisons. The skilled artisan will recognize that the methods and apparatuses discussed above can be configured to more or less accurate depending upon the equipment used and that the choice of equipment can depend on constraints such as monetary constraint and upon the amount of accuracy needed for a particular purpose.

Other Screens

The present invention may be employed by itself or in combination with other screening protocols for the analysis of liquids or their consitituents. Without limitation, examples of such screening techniques include those addressed in commonly-owned U.S. Pat. No. 6,182,499 (McFarland et al); U.S. Pat. No. 6,175,409 B1 (Nielsen et al); U.S. Pat. No. 6,157,449 (Hajduk et al); U.S. Pat. No. 6,151,123 (Nielsen); U.S. Pat. No. 6,034,775 (McFarland et al); U.S. Pat. No. 5,959,297 (Weinberg et al), U.S. Pat. No. 5,776,359 (Schultz et al.), all of which are hereby expressly incorporated by reference herein.

Screening techniques may also include (without limitation) optical screening, infrared screening, electrochemical screening, flow characterization (e.g., gas, liquid or gel-phase chromatography), spectrometry, crystallography, or the like.

It should be understood that the invention is not limited to the exact embodiment or construction, which has been illustrated and described but that various changes may be made without departing from the spirit and the scope of the invention.

What is claimed is:

1. A method for screening an array of materials for surface tension or interfacial tension, the method comprising the steps of:

providing at least four material samples in substantially liquid form;

applying a force to the at least four material samples at a rate of no greater than 10 minutes per sample;

monitoring a response of the at least four material samples to the force; and correlating the response of the at least four material samples to the surface tension or interfacial tension of the at least four material samples.

2. A method as in claim 1 wherein the step of providing at least four material samples includes supporting the at least four material samples with a common singular substrate wherein each of the samples includes a characteristic that makes it different with respect to each of the other samples.

3. A method as in claim 1 wherein the step of applying a force to the at least four material samples includes dispensing at least a portion of each of the at least four material samples in several drops under the force of gravity.

4. A method as in claim 3 wherein the step of monitoring the response of the at least four material samples includes measuring the flowrate of the at least four material samples during dispensing.

5. A method as in claim 1 wherein at least part of the force is applied to the at least four material samples by contacting the material samples with a member.

6. A method as in claim 5 wherein the member is a substrate and the step of applying the force to the at least four material samples includes dispensing a drop of each of the at least four samples upon the substrate.

7. A method as in claim 1 wherein the force is applied to the at least four material samples by expanding a fluid within the at least four sample materials.

8. A method for screening an array of materials for a tension the method comprising the steps of:

providing at least four material samples in substantially liguid form;

applying a force to the at least four material samples at a rate of no greater than 10 minutes per sample wherein the force causes a portion of each of the material samples to separate from itself at a substantially known cross-section;

monitoring a response of the at least four material samples to the force; and correlating the response of the at least four material samples to the tension of the at least four material samples.

9. A method as in claim 8 wherein each of the at least four samples are in substantially liquid form and wherein the tension is selected from surface tension or interfacial tension.

10. A method for screening an array of materials for a tension the method comprising the steps of:

providing at least four material samples in substantially liguid form;

applying a force to the at least four material samples at a rate of no greater than 10 minutes per sample wherein the force is applied substantially entirely by gravity;

monitoring a response of the at least four material samples to the force; and correlating the response of the at least four material samples to the tension of the at least four material samples.

11. A method as in claim 10 wherein each of the at least four samples are in substantially liquid form and wherein the tension is selected from surface tension or interfacial tension.

12. A method for screening an array of materials for tension, the method comprising the steps of:

providing at least four material samples in at least four wells of a substrate, the at least four material samples being different from each other with respect to at least one characteristic, the at least one characteristic being selected from the group consisting of composition, physical condition and temperature;

aspirating the at least four material samples into one or more capillary tubes wherein the step of aspirating the at least four material samples includes employing an automated system with a robot arm for moving the one or more capillary tubes between the at least four wells of the substrate;

dispensing the at least four material samples wherein each of the at least four material samples forms several separate drops during dispensing;

monitoring a response of the at least four material samples during dispensing wherein the monitoring of the response includes monitoring the amount of time for the several separate drops to be dispensed;

correlating the response of the at least four material samples to the tension of the at least four material samples wherein correlating the response includes correlating the amount of time for the drops to be dispensed to the tension of the at least four material samples and wherein the amount of time for the drops to be dispensed is correlated to a flow rate of the at least four samples during dispensing, which in turn is related to the tension of the at least four material samples.

13. A method as in claim 12 wherein one of the at least four material samples is dispensed within 2 minutes of another of the at least four material samples.

14. A method for screening an array of materials for tension, the method comprising the steps of:

providing at least four material samples, the at least four material samples being different from each other with respect to at least one characteristic;

aspirating the at least four material samples into one or more capillary tubes;

dispensing the at least four material samples;

monitoring a response of the at least four material samples during or after dispensing, the response being selected from a contact angle of the at least four material samples and a flowrate of the at least four material samples during dispensing; and correlating the response of the at least four material samples to the tension of the at least four material samples.

15. A method as in claim 14 wherein the step of providing at least four material samples includes supporting the at least four material samples with a common singular substrate.

16. A method as in claim 14 wherein the step of applying a force to the at least four material samples includes dispensing at least a portion of each of the at least four material samples in several drops under the force of gravity.

17. A method as in claim 16 wherein the step of monitoring the response of the at least four material samples includes measuring the flowrate of the at least four material samples during dispensing.

18. A method as in claim 14 wherein the step of dispensing the at least four material samples includes dispensing a drop of each of the at least four samples upon a substrate.

19. A method as in claim 14 wherein the material samples are dispensed such that drops of the material samples separate from themselves at a substantially known cross-section.

20. A method as in claim 14 wherein the at least four material samples are dispensed substantially entirely under only a force provided by gravity.

21. A method as in claim 14 wherein one of the at least four material samples is dispensed within 10 minutes of another of the at least four material samples.

22. A method as in claim 14 wherein one of the at least four material samples is dispensed within 2 minutes of another of the at least four material samples.

23. A method as in claim 14 wherein each of the at least four samples are in substantially liquid form and wherein the tension is selected from surface tension or interfacial tension.

* * * * *

UNITED STATES PATENT AND TRADEMARK OFFICE
CERTIFICATE OF CORRECTION

PATENT NO. : 6,857,309 B2
DATED : February 22, 2005
INVENTOR(S) : Paul Mansky It is certified that error appears in the above-identified patent and that said Letters Patent is hereby corrected as shown below:

Column 19,
Lines 18 and 37, replace "liguid" with -- liquid --.

Signed and Sealed this

Twelfth Day of July, 2005

JON W. DUDAS
*Director of the United States Patent and Trademark Office*